(12) United States Patent
Hesch

(10) Patent No.: US 6,451,779 B1
(45) Date of Patent: Sep. 17, 2002

(54) COMPOSITION AND METHOD FOR CONTRACEPTION AND TREATMENT OF TUMORS OF THE MAMMARY GLANDS

(76) Inventor: Rolf-Dieter Hesch, Alpsteinweg 8, D78464, Kosntanz (DE)

( * ) Notice: Subject to any disclaimer, the term of this patent is extended or adjusted under 35 U.S.C. 154(b) by 0 days.

(21) Appl. No.: 09/403,673
(22) PCT Filed: Feb. 12, 1998
(86) PCT No.: PCT/DE98/00428
§ 371 (c)(1),
(2), (4) Date: Apr. 11, 2000
(87) PCT Pub. No.: WO98/35682
PCT Pub. Date: Aug. 20, 1998

(30) Foreign Application Priority Data

Feb. 12, 1997 (DE) .......................................... 197 05 229

(51) Int. Cl.[7] .............................................. A61K 31/56
(52) U.S. Cl. ........................ 514/171; 424/422; 424/426; 424/430; 424/435; 424/436; 424/448; 424/449
(58) Field of Search .................................. 424/448, 449, 424/422, 426, 430, 435, 436; 514/171

(56) References Cited

FOREIGN PATENT DOCUMENTS

DE          43 08 406 C1       6/1994

*Primary Examiner*—Jose' G. Dees
*Assistant Examiner*—Michael A. Williamson
(74) *Attorney, Agent, or Firm*—Knobbe, Martens, Olson & Bear, LLP

(57) ABSTRACT

A composition with three hormone components is administered to a mammal to cause the suppression or cessation of the menstruation cycle. Alternatively, it can be administered for treatment of tumors of the mammary gland. The composition contains at least a synthetic estrogen, a biogenetic estrogen, and a gestagen. Alternatively, the composition can include hormones which upon ingestion are metabolized to the above-mentioned hormones.

17 Claims, No Drawings

COMPOSITION AND METHOD FOR CONTRACEPTION AND TREATMENT OF TUMORS OF THE MAMMARY GLANDS

This is the U.S. National Phase under 35 U.S.C. §371 of International Application PCT/DE98/000428, filed Feb. 12, 1998, which claims priority of German Application DE 19705229.0-41, filed Feb. 12, 1997.

The invention relates to a means for hormonal contraception with three components used especially for the treatment and/or prophylaxis of tumors of the mammary glands, as well as a process for the hormonal contraception and/or treatment and/or prophylaxis of tumors of the mammary glands.

Since the beginning of the availability of hormonal contraceptives in the 1960s, a large number of hormonal components were developed with regard to their suitability in very different administration schemes. Basically, a division into combination and sequence preparations is possible.

In known combination preparations, for example, in as far as the desired cycle period is 28 days, a combination of an estrogen and a gestagen preparation is administered for 21 days in a constant or changing, absolute or relative dosage, wherein the estrogen preparation can be, for example, natural estrogen or synthetic ethinylestradiol and a 7-day pause follows the ingestion of the above-mentioned 21 daily units during which time a withdrawal bleeding occurs simulating the natural monthly bleeding.

In the known sequence preparations, also in a desired cycle period of 28 days, a pure estrogen preparation is administer for 7 days and then for 15 days a combination of an estrogen preparation and a gestagen preparation, wherein also here an ingestion-free period of, for example, 6 days follows during which time a withdrawal bleeding occurs. Although it is known to bridge the period of ingestion pause of the combination and sequence preparations in the interest of a greater ingestion safety by administering placebos within those specific days, this was always based on the notion that during the approximately one-week long ingestion period no hormones of the here discussed type may be administered in order to guarantee a reliable withdrawal bleeding. Only in substitution preparations in the menopause of the older women were hormones administered during the total cycle, for example in the sequence of estrogen preparation for 10 days, combination of estrogen and gestagen preparation for 11 days, estrogen preparation for 7 days in especially low dosage; however, these substitution preparations are not suitable for the stopping of ovulation.

The sequence preparations used in substitution therapy are especially unsuitable for contraception because the natural estradiol in the given dosage does not prevent ovulation and the phase in which gestagen is administered is, at 11 days, too short. The below described sequential order guarantees in substitution preparations, however, a relatively good cycle control.

From DE-PS 43 08 406, a combination preparation for contraception is known consisting of one or more steps. In so doing, it is provided that at least one step contains the combination of three components, namely a biogenetic estrogen, a synthetic estrogen and a gestagen and the further steps consists of a pharmaceutically unobjectionable placebo or a biogenetic or synthetic gestagen, or a biogenetic or synthetic estrogen, or a combination of three components, namely a biogenetic estrogen, a synthetic estrogen and a gestagen or a combination of synthetic estrogens and a gestagen.

From the description of the above publication is can be seen that, with the step concept described therein, a change in condition occurs typically over time. Such a change in condition can also occur in such a way that the putting together of the phases that constitute the step can be changed in terms of the employed components, as well as by only changing the concentrations of the components employed in the phases that make up the step.

Even when only one single step without component change is provided as provided by a special embodiment of the combination preparation according to DE-PS 43 08 406, one proceed in any case in a way that a withdrawal bleeding occurs because, after the complete disclosure of DE-PS 43 08 406, such a withdrawal bleeding is considered indispensable for the achievement of the desired contraceptive safety.

It is the object of the invention to make available a means for hormonal contraception which offers a high contraceptive safety and eliminates intermediary bleedings. Furthermore, the side-effects otherwise observed in hormonal means of contraception should be further reduced.

In so doing, especially also an effective treatment and/or prophylaxis of tumors of the mammary glands should be make possible.

According to the invention, this problem is solved by a means for hormonal contraception with three components containing a first hormone component with at least one synthetic estrogen, a second hormone component with at least one biogenetic estrogen, and a third hormone component with at least one gestagen for continuous and combined administration.

Finally, the problem is solved through a process for hormonal contraception which provides that a means having at least one first hormone component with at least one synthetic estrogen, a second hormone component with at least one biogenetic estrogen, and a third hormone component with at least one gestagen be continuously administered.

In a further aspect, the invention relates to the use of the means of stopping ovulation according to the invention.

In still a further aspect, the invention relates to the use of the means according to the invention for the treatment and/or prophylaxis of tumors of the mammary glands.

In so doing, it can be provided that the synthetic estrogen is selected from a group consisting of ethinylestradiol, mestranol and others, as well as hormone combinations which quickly split off at least one synthetic estrogen upon ingestion.

In a preferred embodiment it is provided that the synthetic estrogen is ethinylestradiol.

In a completely preferred embodiment it is provided that the daily administered amount of ethinylestradiol is from 1 to 20 µg.

In so doing, it is even more preferred that the daily administered amount of ethinylestradiol is from 5 to 10 µg.

According to the invention, it can be further provided that the second hormone component is selected from a group consisting of estradiol, estriol, estrone, estran and others, as well as hormone combinations which quickly split off at least one of the mentioned estrogens upon ingestion.

In a preferred embodiment it is provided that the second hormone component consists of 17-α-estradiol and/or 17-β-estradiol.

In a further embodiment of the means according to the invention, it can be provided that the daily administered amount of second hormone component is in the case of estradiol, especially α- and β-estradiol from 0.1 to 2 mg and in the case of conjugated estrogen it is from 0.05 to 0.5 mg.

In a further embodiment of the means according to the invention, a third hormone component is selected from a group consisting of progesterone, chlormadinone acetate, norethisterone acetate, cyproterone acetate, desogestrel, levonorgestrel and other natural and/or synthetic gestagens as well as hormone combinations which quickly split off at least one of the mentioned gestagens upon ingestion.

In an embodiment, the means according to the invention can be provided for oral administration.

In an alternative embodiment, the means according to the invention can be provided for transdermal administration.

In a second alternative embodiment, the means according to the invention can be provided for intravaginal administration.

In a third alternative embodiment, the means according to the invention can be provided as depository injection.

In a fourth alternative embodiment, the means according to the invention can be provided as a hormone implant.

Finally, it can be provided that the daily units which each contain all three hormone components are arranged as spacially separated and individually dispensable in a packaging unit.

In an embodiment of the process according to the invention it can finally be provided that the means according to the invention are administered.

Providing the basis for the invention is a surprising notion that high contraceptive safety can be realized through continuous and combined administration of a means consisting of three hormone components, namely a first hormone component with at least one synthetic estrogen, a second hormone component with at least one biogenetic estrogen, and a third hormone component with at least one gestagen. By continuous administration, understood here is an administration that is uninterrupted over the application period in which there are no ingestion-free intervals in regard to the hormone components. This also means that the interruption of the administration of the means through the giving of placebos instead of the hormonal means is not provided. Consequentially, there are over the total time period which is typically from several months to years no changes in the basic composition of the hormone components. Instead of this, the hormone components which form the hormonal means according to the invention are administered at unchanged concentration over the total period of administration in an uninterrupted and unchanged manner. It is thinkable that the concentration of biogenetic estrogens and gestagens are unchanged in older women in contrast to younger women. This can also occur in such a way that during the continuous application one first begins with a certain composition and it is then adjusted in over weeks, months and years to the changed biological requirements of the women through the application of a follow-up preparation.

As a result of the continuous application of the mentioned hormone components, it is guaranteed that the naturally occurring hormonal processes in the female organism do not compromise the contraceptive safety.

Furthermore, dependent on the persisting estrogen supply, this leads to a generally positive blood vessel-expanding effect through which circulation problems can be counteracted. Also, through the means according to the invention, the fluctuations, observed according to the state of art, in the hormone level resulting from the intake of hormonal means for contraception especially the estrogen component associated side-effects in the form of so-called premenstrual syndrome are subdued.

The balanced estrogen level achieved in such a manner also avoids the decrease and increase again of coagulation parameters, on corresponding means according to the state of the art, during the observed hormone-free days or after re-initiation of intake in the next cycle, through which among others the coagulation system, which is in an unstable equilibrium, is otherwise disturbed. Therefore the hormonal means according to the invention is especially suitable for women of more than 40 years in whom the danger of circulation problems is known to increase with increased age. Also, the danger of thrombosis which has recently reached significant importance in contraceptive therapy is largely reduced.

Surprisingly, it has also been found that with the administration of the means, according to the invention, reliably a continuous suppression of the menstruation cycle and the monthly bleeding at decidedly lower dosage is possible. Without wanting to be limited to it in the following, it seems that the combination of the mentioned hormone components, and especially the small dosage of estrogens therein, is suitable for eliminating the otherwise common side-effects of ethinylestradiol and to cut the dosages of more than 15 $\mu$g of ethinylestradiol otherwise typically required in contraceptives according to the state of the art.

Finally, the hormonal means for contraception according to the invention guarantees the prevention of an endogenetic hormone deficit through substitution. Such a endogenetic hormone deficit is observed in the hormonal contraceptives according to the state of the art as a result of the suppressive effect of ethinylestradiol, whereas the ethinylestradiol which in a series of hormonal contraceptives is given at a comparatively low dosage is not able to balance out this deficit, and therefore this leads to the common hormone deficit occurrences up to the polycystic ovaries.

The low dosage of the individual hormone components, and especially of the estrogen component(s), is made possible by the additive effect of the hormone components without that it leads to a reduction of the effect of the means according to the invention in regard to its contraceptive as well as ovulation-stopping characteristics.

The ovulation stoppage and suppression of the menstrual cycle reliably guaranteed through the means according to the invention is of high importance for certain patients such as, for example, for professional female athletes, female dancers and business women who want to eliminate the reduction in the physical, mental and emotional fitness brought about by the menstrual cycle.

As a result of the combined and continuous administration of the three hormone components of the means according to the invention it is possible to administer it either orally, transdermally, intravaginally, through depository injections or hormone implants. In so doing, advantages observed for the individual application forms can be realized also in the present case.

As oral administration forms, all known forms of the state of the art such as, for example, tablets, sugarcoated or non-sugarcoated pills, or capsules which are manufactured using the usual auxilliary- and carrier agents.

In the transdermal administration of the means according to the invention, the three hormone components that form the means can be placed, for example, on a plaster or also applied by means of transdermal therapeutic systems and thus are administer to the organism, whereas, for example, an already prepared combination of the three hormone components or these individually are introduced into such a system which is based on iontophoresis or diffusion or, optionally, a combination of these effects.

For the case of oral application, it has proven to be sensible that the daily units that each contain the combination of the three hormone components are arranged as spacially separated and individually dispensable in a packaging unit, such that the easy control of whether or not the typical daily oral preparation to be taken has already been taken is possible. In so doing, it is important that it is guaranteed that no intake-free days occur. Depository injections can be applied every 1 to 6 months or longer; hormone implants contain all three hormone components and give these off over the period of preferably from 3 to 6 months.

In so doing, in the use of the means according to the invention, it has been surprisingly shown that the treatment and/or prophylaxis of tumors of the mammary glands is possible. It is an understanding of recent research into breast cancer risk that it is set through mutations that occur in certain risk genes which can be inherited or acquired. Modern cancer theory is based on the notion that a cancer-triggering mutation is present on one of both alleles of a gene which at first is still controlled by the other healthy allele. If, over the course of lifetime, a further mutation in a certain cell of an organ appears also on the second allele, then this can transformed into an uncontrolled malignant growth.

Mutations on the second allele appear especially often at certain phases of the cell cycle, namely in the so-called G1-phase. The menstruation cycle leads the breast cell into a cell cycle every 4 weeks, "opens" the genome for mutations which are either repaired or apoptotically "cleared off." Under the conditions of the classical combined or sequential contraception treatment, a woman can have from 500 to 700 cycles over the course of her lifetime, while under "natural conditions" a woman has a maximum of 20 to 30 cycles. Thus an unusually high number of cell cycles over a period of 8 days brings a large mutation risk into the stimulated mammary gland tissue. If the menstruation cycle is suppressed, as it is possible with the means according to the invention, then the breast cells are brought into a "resting phase" and it is scientifically ensured that, in the resting phase, fewer cancer-triggering mutations enter into a tissue than into a stimulated tissue. Thus, mutagenesis, that is, the breast cancer risk is reduced by a large amount.

In the case of the present invention, biogenetic estrogens are also those produced by the human body and thus include body-own estrogens. The biogenetic estrogens used in the means according to the invention are typically those synthesized chemically. Basically, however, also the use of such compounds isolated from an organism is possible.

By biogenetic estrogens should be understood, in the present case, also conjugated biogenetic estrogens such as, for example, estradiol valerate or estrone sulfate.

The amount of the administered gestagen corresponds to the amount of comparable preparations according to the state of the art.

In the following, the invention is explained in detail using embodiment examples.

EXAMPLE 1

For the contraceptive treatment, a means was used which, per daily unit in tablet form, contained 5 μg of ethinylestradiol, 0.5 mg of 17-β-estradiol and 1 mg of norethisterone acetate. The means was administered over a period of 9 months and demonstrated very high contraceptive safety at a complete suppression of the menstruation cycle and practically no side-effects. Within the framework of the investigation introduced here, it was ensured that the participants took the means daily, that is, without intake pause over the entire above-mentioned time period.

EXAMPLE 2

For the prophylaxis of tumors of the mammary glands, at simultaneous maintenance of a high contraceptive safety, a means was used which, per daily unit in tablet form, contained 10 μg of ethinylestradiol, 1.0 mg of 17-β-estradiol and 2 mg of chlormadinone acetate. The means was administered over a period of 12 months without an intake pause. The mode of action corresponded to that in Example 1.

EXAMPLE 3

For the contraceptive treatment, a means was used which, per daily unit in tablet form, contained 10 μg of ethinylestradiol, 0.5 mg of estriol and 1 mg of norethisterone acetate. The means was administered over a period of 12 months without an intake pause. The mode of action corresponded to that in Example 1.

EXAMPLE 4

For the contraceptive treatment, a means was used which, per daily unit in tablet form, contained 10 μg of ethinylestradiol, 0.5 mg of estriol and 2 mg of chlormadinone acetate. The means was administered over a period of 12 months without an intake pause. The mode of action corresponded to that in Example 1.

EXAMPLE 5

For the contraceptive treatment, a means was used which, per daily unit in tablet form, contained 10 μg of ethinylestradiol, 0.1 mg of estradiol valerate and 1 mg of norethisterone acetate. The means was administered over a period of 12 months without an intake pause. The mode of action corresponded to that in Example 1.

What is claimed is:

1. A method for hormonal contraception comprising administering to a mammal: a composition comprising at least one synthetic estrogen, at least one biogenetic estrogen, and at least one gestagen wherein said at least one synthetic estrogen, said at least one biogenetic estrogen, and said at least one gestagen are administered continuously at unchanged concentrations to result in continuous suppression of the menstrual cycle.

2. The method according to claim 1 wherein the synthetic estrogen is selected from the group consisting of: ethinylestradiol, and mestranol.

3. The method according to claim 2 wherein the synthetic estrogen is ethinylestradiol.

4. The method according to claim 3 wherein the daily administered amount of ethinylestradiol is from 1 to 20 ug.

5. The method according to claim 4 wherein the daily administered amount of ethinylestradiol is from 5 to 10 ug.

6. The method according to claim 1 wherein the biogenetic estrogen is selected from the group consisting of estradiol, estriol, estrone, and estran.

7. The method according to claim 1 wherein the second hormone component is selected from the group consisting of 17-α-estradiol, 17-β-estradiol, and both.

8. The method according to claim 7, wherein the daily administered amount of the α- and β-estradiol is from about 0.1 to 2 mg.

9. The method according to claim 1, wherein the third hormone component comprises a natural or synthetic gestagen.

10. The method according to claim 1 wherein said method is for oral administration.

11. The method according to claim 1 wherein said method is for transdermal administration.

12. The method according to claim 1 wherein said method is for intravaginal administration.

13. The method according to claim 1 wherein said method is administered as a depository injection.

14. The method according to claim 1 wherein said method is administered as hormone implant.

15. The method according to claim 1, wherein the daily units comprise all three hormone components and wherein said daily units are arranged as spacially separated and individually dispensable in a packaging unit.

16. The method of claim 1 wherein said method stops ovulation.

17. The method according to claim 1, wherein the gestagen is selected from the group consisting of progesterone, chlormadinone acetate, norethisterone acetate, cyproterone acetate, desogestrel, levonorgestrel.

* * * * *